(12) United States Patent
Fingerhut

(10) Patent No.: US 9,033,994 B2
(45) Date of Patent: May 19, 2015

(54) BONE GRAFT DELIVERY DEVICE

(71) Applicant: SpineSmith Partners, L.P., Austin, TX (US)

(72) Inventor: Rebecca Fingerhut, League City, TX (US)

(73) Assignee: SpineSmith Partners, L.P., Austin, TX (US)

( * ) Notice: Subject to any disclaimer, the term of this patent is extended or adjusted under 35 U.S.C. 154(b) by 76 days.

(21) Appl. No.: 13/666,701

(22) Filed: Nov. 1, 2012

(65) Prior Publication Data

US 2013/0190718 A1    Jul. 25, 2013

Related U.S. Application Data

(60) Provisional application No. 61/554,790, filed on Nov. 2, 2011.

(51) Int. Cl.
| | | |
|---|---|---|
| A61B 17/58 | (2006.01) | |
| A61B 17/60 | (2006.01) | |
| A61F 2/00 | (2006.01) | |
| A61B 17/88 | (2006.01) | |
| A61F 2/46 | (2006.01) | |
| A61F 2/44 | (2006.01) | |
| A61F 2/28 | (2006.01) | |

(52) U.S. Cl.
CPC ........... *A61B 17/8805* (2013.01); *A61F 2/4601* (2013.01); *A61F 2/447* (2013.01); *A61F 2002/2835* (2013.01); *Y10S 606/914* (2013.01)

(58) Field of Classification Search
CPC ........ A61F 2/46; A61F 2/4601; A61F 2/4611
USPC ............................................. 606/99, 100, 914
See application file for complete search history.

(56) References Cited

U.S. PATENT DOCUMENTS 6,652,533 B2 * 11/2003 O'Neil ......................... 606/100

* cited by examiner

*Primary Examiner* — Andrew Yang
(74) *Attorney, Agent, or Firm* — Winstead PC

(57) ABSTRACT

Aspects of the claimed invention relate generally to devices for delivering bone graft compositions to implants that have been positioned between vertebral bodies during surgery and methods of using such devices. Embodiments of the invention provide ease of bone graft delivery in situ while providing an environment for the mixing of bone graft, insertion of the bone graft, and packing of the graft into the voids above and below the implant.

4 Claims, 4 Drawing Sheets

BONE GRAFT DELIVERY DEVICE

CROSS-REFERENCES TO RELATED APPLICATIONS

This Application claims the benefit under 35 U.S.C. §119 (e) of U.S. Provisional Patent Application Ser. No. 61/554,790, filed Nov. 2, 2011, which is incorporated herein by reference in its entirety as if fully set forth herein.

FIELD OF THE INVENTION

The claimed invention relates generally to devices for delivering bone graft compositions to implants that have been positioned between vertebral bodies during surgery.

BACKGROUND OF THE INVENTION

With the arrival of new open face interbody implant designs for implantation between vertebrae, there is a new need for packing bone graft in situ. Currently, bone graft is packed into the middle of the interbody implants before insertion. This does not allow the graft from the center of the implants to reach above and below the implant to the concave voids created by the nature of the endplates. With the new open face designs, bone graft is packed in situ allowing the graft to reach these endplates. Due to the nature of some spinal surgeries, there is often a large distance from the incision to the disc space making addition of bone graft material difficult while in-situ. Currently, funnels or forceps are used to aid in the delivery bone graft in situ which requires the use of a mixing container, a funnel or forceps for insertion and forceps or tamp for movement of the mixture in situ to the desired packing. Funnels, particularly, reduce visibility of the space with the relatively small incisions made. Additionally, syringes for creation of bone logs are also known. Thus, there exists a need for ease of graft delivery in situ while providing an environment for the mixing of bone graft, insertion of the bone graft, and packing of the graft into the voids above and below the implant.

SUMMARY OF THE INVENTION

An embodiment of the invention is directed to a device for delivering bone graft material to an implant during surgery, comprising: an elongate handle which comprises a cannulated outer rod and an inner rod having a distal end and a proximal end, a footplate connected to the distal end of the inner rod, and a removable cartridge configured to enclose the footplate and distal end of the inner rod such that the cartridge becomes removably connected to the distal end of the inner rod and the footplate.

A further embodiment of the invention is directed to a process for producing a device for delivery of bone graft material to an implant during surgery, comprising: providing an elongate handle which comprises a cannulated outer rod and an inner rod having a distal end and a proximal end, providing a footplate connected to the distal end of the inner rod, providing a removable cartridge configured to enclose the footplate and distal end of the inner rod so that the cartridge becomes removably connected to the distal end of the inner rod and the footplate.

DETAILED DESCRIPTION OF EXEMPLARY EMBODIMENTS OF THE INVENTION

An embodiment of the invention provides a device for ease of graft delivery in situ while providing an environment for the mixing of bone graft, insertion of the bone graft, and packing of the graft into the voids above and below the implant. Aspects of the invention also allow for clotting of the mixture to occur before insertion into the disc space by having a cartridge that takes on the approximate shape and size needed. This cannot be done using a funnel. Additionally, the cartridge and proximal hole that the substrate-agent mix is being pushed through is the approximate size of the void that is being filled making the tamping action minimal to avoid disruption of the bone graft material. The tamping action that can be done with the claimed device allows for some movement of the substrate-agent mix in the disc space to fill the concave voids at each endplate creating the contact needed. Furthermore, the device locates to the implant and remain in place for ease of delivery of bone graft.

An embodiment of the invention is directed to a device for delivering bone graft material to an implant during surgery, comprising: an elongate handle which comprises a cannulated outer rod and an inner rod having a distal end and a proximal end, a footplate connected to the distal end of the inner rod, and a removable cartridge configured to enclose the footplate and distal end of the inner rod such that the cartridge becomes removably connected to the distal end of the inner rod and the footplate.

Figure 1:
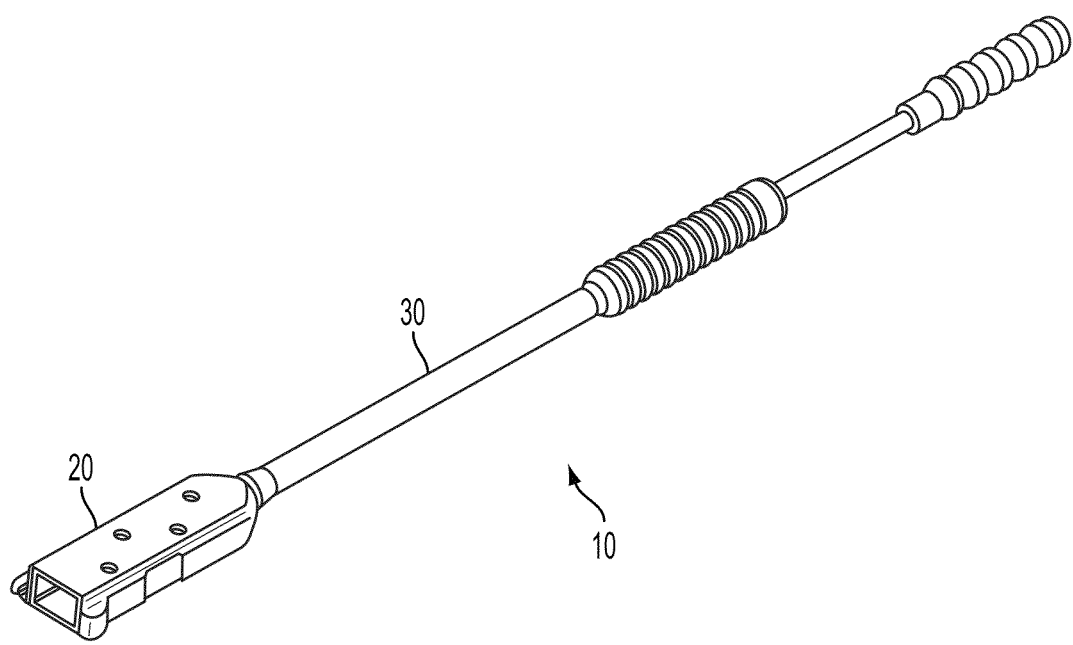
FIG. 1 shows a bone graft delivery device in accordance with an embodiment of the invention.

Referring to FIG. 1, an embodiment of the device 10 is comprised of a cartridge 20 and a plunger construct 30. The cartridge 20 may optionally be pre-packed with an osteoconductive substrate.

Figure 2:
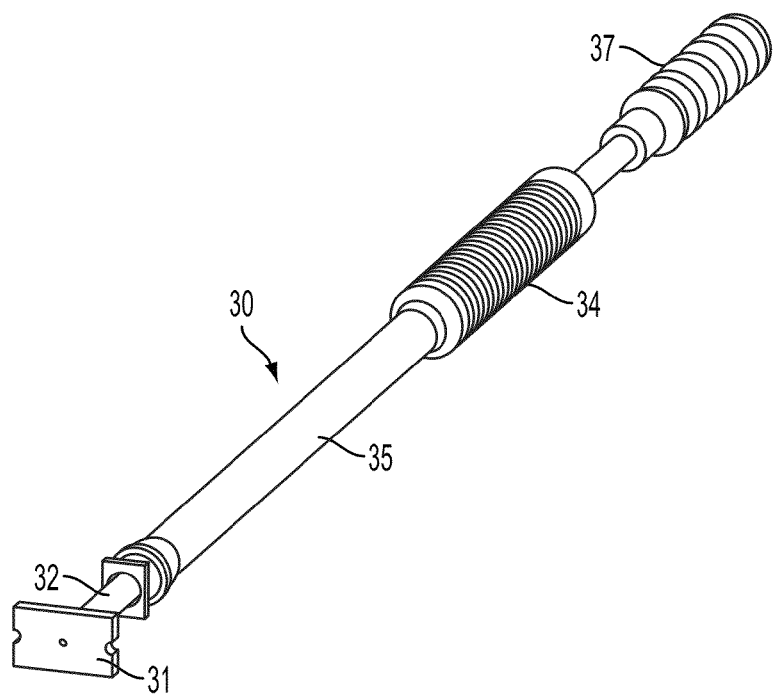
FIG. 2 shows a plunger construct of a bone graft delivery device in accordance with an embodiment of the invention.

As seen in FIG. 2, the plunger construct 30 comprises an inner shaft 32 having a handle 37 and foot plate 31 that takes on the form of a bone tamp and an outer sheath 35 with handle 34. The outer shaft is cannulated to allow the inner shaft to run freely through. In certain embodiments of the invention, the cartridge and plunger construct may come as two separate components that can be assembled in the operating room.

Figure 3:
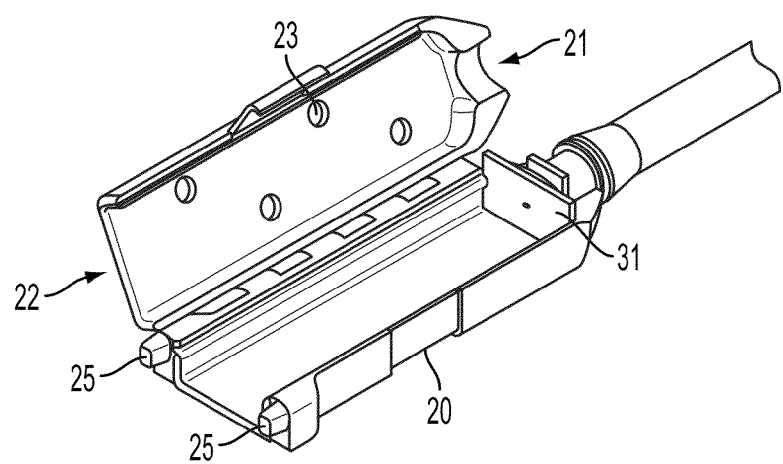
FIG. 3 shows a cartridge of a bone graft delivery device in accordance with an embodiment of the invention.

In certain embodiments of the invention, the cartridge 20 can optionally be hinged on one side as depicted with a snap lock mechanism on other type of fastener or clasp. As shown in FIG. 3, the proximal 21 and distal 22 ends of the cartridge 20 are open to allow the inner shaft 32 of the plunger construct 30 with footplate 31 to move through the cartridge. The cartridge 20 is opened for the attachment of the plunger construct 30 at the distal end 22 of the cartridge 20 and any substrates and/or liquid agents to be added proximal to the retracted footplate 31. The outer shaft 35 and footplate 31 of the plunger construct 30 are captured when the cartridge is closed and snapped shut. This provides a rigid handle for the cartridge, the outer shaft, and a free moving plunger, the inner shaft and footplate. Although liquid agents can be added to the cartridge before snapping shut, there are optional small holes 23 located on the top side of the cartridge to allow for addition of liquid agent just prior to insertion. The holes 23 are located to allow for the liquid agents to soak through the entire substrate. Optional guiding posts 25 protrude at the proximal end to aid in placement of the device adjacent to the face of the implant.

Another embodiment of the invention is directed to a process for producing a device for delivery of bone graft material to an implant during surgery, comprising: providing an elongate handle which comprises a cannulated outer rod and an inner rod having a distal end and a proximal end, providing a footplate connected to the distal end of the inner rod, providing a removable cartridge configured to enclose the footplate and distal end of the inner rod so that the cartridge becomes removably connected to the distal end of the inner rod and the footplate.

A further embodiment of the invention provides a method of delivering bone graft material to a vertebral implant having an open face during surgery, comprising: providing a device for delivering bone graft material, positioning bone graft material in the cartridge, coupling the cartridge to the distal end of the inner rod and the footplate; advancing the inner rod through the outer rod to push the bone graft material into an implant with an open face that is positioned between two vertebral bodies; and optionally tamping the bone graft material.

Figure 4:
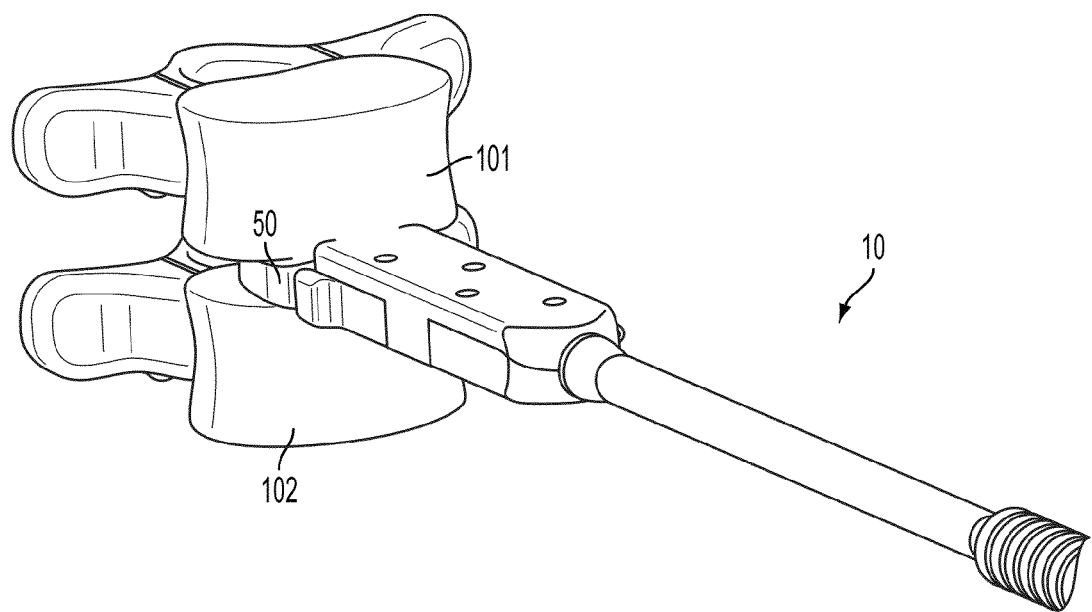
FIG. 4 shows the coupling of an implant and a bone graft delivery device in accordance with an embodiment of the invention.
Figure 5:
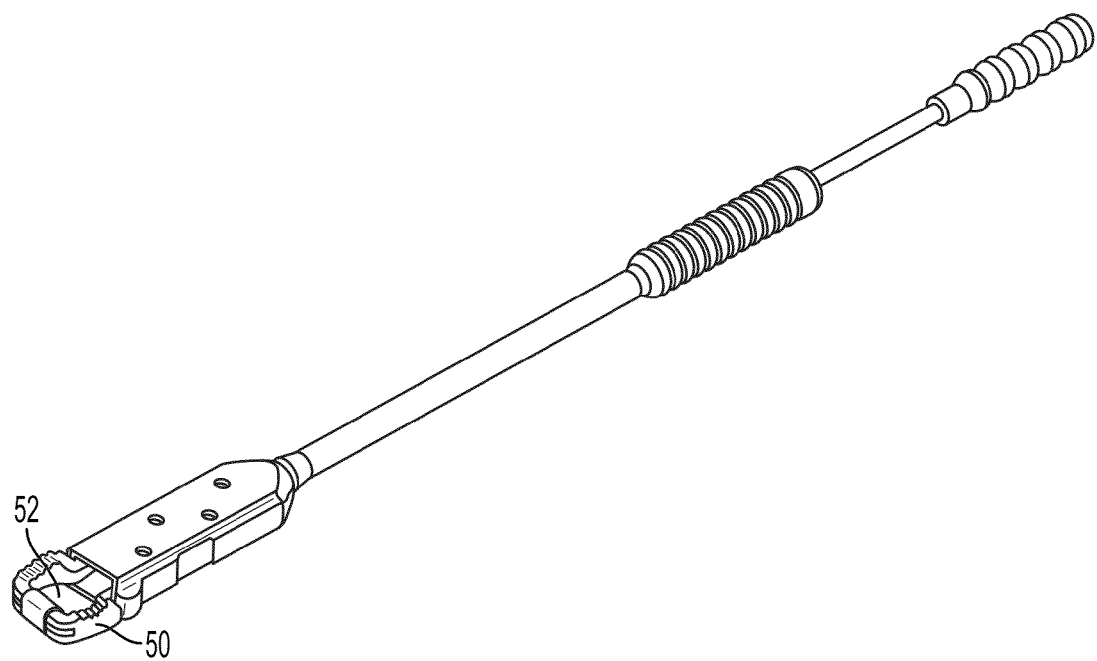
FIG. 5 shows the coupling of an implant and a bone graft delivery device in accordance with an embodiment of the invention.

During use, the inner shaft with handle is pushed or tamped to advance the footplate through the cartridge thereby moving the substrate-agent mix into the distracted disc space. As shown in FIGS. 4-5, the delivery device is configured to couple to an implant 50 having an open face and inner void. FIG. 4 illustrates an implant that is placed between two vertebrae 101, 102 during surgery and the delivery device 20 being inserted and coupled to the implant 50 prior to advancing the plunger to force the graft material into the void 52 of the implant 50. FIG. 5 depicts an non-obscured view of the coupling of the device 10 with the implant 50. The device of this invention can be used, for example, with any implant that can fit between two vertebrae.

After the disc space is filled with the implant, the graft delivery device is removed and can be taken apart in the same fashion as it was put together for cleaning or re-use of the plunger construct. The cartridge and the plunger construct may optionally be disposable. While the invention may be adaptable to various modifications and alternative forms, specific embodiments have been shown by way of example and described herein.

However, it should be understood that the invention is not intended to be limited to the particular forms disclosed. Rather, the invention is to cover all modifications, equivalents, and alternatives falling within the spirit and scope of the invention as defined by the appended claims. Moreover, the different aspects of the disclosed methods and systems may be utilized in various combinations and/or independently. Thus the invention is not limited to only those combinations shown herein, but rather may include other combinations.

What is claimed is:

1. A device for delivering bone graft material to an implant during surgery, comprising:
    an elongate handle which comprises a cannulated outer rod and an inner rod having a distal end and a proximal end, wherein the cannulated outer rod includes at least one guide pin on the distal end;
    a footplate connected to the distal end of the inner rod, and
    a removable cartridge configured to enclose the footplate and distal end of the inner rod such that the cartridge becomes removably connected to the distal end of the inner rod and the footplate.

2. The device of claim 1 wherein the cartridge includes two hinged members.

3. The device of claim 1, wherein the cartridge includes holes on one face.

4. A method of delivering bone graft material to a vertebral implant having an open face during surgery, comprising:
    providing the device of claim 1,
    positioning bone graft material in the cartridge,
    coupling the cartridge to the distal end of the inner rod and the footplate;
    advancing the inner rod through the outer rod to push the bone graft material into an implant with an open face that is positioned between two vertebral bodies; and
    optionally tamping the bone graft material.

* * * * *